United States Patent
Tol et al.

(10) Patent No.: US 9,597,506 B2
(45) Date of Patent: Mar. 21, 2017

(54) SYSTEM FOR NEUROSTIMULATION AND/OR NEURORECORDING

(71) Applicant: Medtronic Bakken Research Center B.V., Maastricht (NL)

(72) Inventors: Jeroen Jacob Arnold Tol, Eindhoven (NL); Egbertus Johannes Maria Bakker, Wijk en aalburg (NL)

(73) Assignee: Medtronic Bakken Research Center B.V., Maastricht (NL)

( * ) Notice: Subject to any disclaimer, the term of this patent is extended or adjusted under 35 U.S.C. 154(b) by 0 days.

(21) Appl. No.: 14/952,783

(22) Filed: Nov. 25, 2015

(65) Prior Publication Data

US 2016/0144185 A1 May 26, 2016

Related U.S. Application Data

(60) Provisional application No. 62/084,336, filed on Nov. 25, 2014.

(51) Int. Cl.

| | | |
|---|---|---|
| *A61N 1/00* | (2006.01) | |
| *A61N 1/36* | (2006.01) | |
| *A61M 5/00* | (2006.01) | |
| *A61N 1/08* | (2006.01) | |
| *A61M 5/172* | (2006.01) | |
| *A61M 5/142* | (2006.01) | |
| *A61N 1/05* | (2006.01) | |

(52) U.S. Cl.
CPC .......... *A61N 1/36125* (2013.01); *A61M 5/00* (2013.01); *A61M 5/14276* (2013.01); *A61M 5/1723* (2013.01); *A61N 1/08* (2013.01); *A61N 1/36128* (2013.01); *A61M 2205/50* (2013.01); *A61M 2205/82* (2013.01); *A61N 1/0534* (2013.01); *A61N 1/36064* (2013.01); *A61N 1/36067* (2013.01); *A61N 1/36082* (2013.01)

(58) Field of Classification Search
CPC ......... A61N 1/36128–1/3616; A61N 1/37211; A61N 1/37288; A61N 1/08; A61N 1/36125; A61M 5/00; A61M 5/14276; A61M 5/1723; A61B 5/04
See application file for complete search history.

(56) References Cited

U.S. PATENT DOCUMENTS

| | | |
|---|---|---|
| 4,583,865 A | 4/1986 | Kirk et al. |
| 6,516,808 B2 | 2/2003 | Schulman |
| 7,013,178 B2 | 3/2006 | Reinke et al. |
| 7,079,977 B2 | 7/2006 | Osorio et al. |
| 7,941,202 B2 | 5/2011 | Hetke et al. |

(Continued)

FOREIGN PATENT DOCUMENTS

WO 2010055453 A1 5/2010

*Primary Examiner* — Scott Getzow
(74) *Attorney, Agent, or Firm* — Shumaker & Sieffert, P.A.

(57) ABSTRACT

The disclosure describes devices, systems, and techniques for checking synchronization between two or more modules of a system. In one example, a first module is configured to output a therapy, and a second module distinct from the first module is configured to receive an alternating current (AC) power signal from an AC power source, monitor a characteristic of the AC power signal, determine, based on the characteristic of the AC power signal, a period of time during which the first module is expected to one of output the therapy or refrain from outputting the therapy, and check, during the period of time, a synchronicity between the first module and the second module.

28 Claims, 8 Drawing Sheets

(56) References Cited

U.S. PATENT DOCUMENTS

| | | |
|---|---|---|
| 2003/0149456 A1 | 8/2003 | Rottenberg et al. |
| 2010/0106220 A1 | 4/2010 | Ecker et al. |
| 2015/0091533 A1 | 4/2015 | Blanken et al. |

SYSTEM FOR NEUROSTIMULATION AND/OR NEURORECORDING

This application claims priority to U.S. Provisional Patent Application No. 62/084,336, entitled "SYSTEM FOR NEUROSTIMULATION AND/OR NEURORECORDING" and filed Nov. 25, 2014, the entire contents of which is incorporated herein by reference.

TECHNICAL FIELD

The disclosure relates to electrical stimulation systems and, more particularly, communication between modules of an electrical stimulation system.

BACKGROUND

Implantable neurostimulation devices have been used for the past several years to treat acute or chronic neurological conditions. Deep brain stimulation (DBS), the mild electrical stimulation of sub-cortical structures, belongs to this category of implantable devices and has been shown to be therapeutically effective for Parkinson's disease, Dystonia, Essential Tremor, Obsessive Compulsive Disorder, and Epilepsy. New applications of DBS in the domain of psychiatric disorders (clinical depression, anorexia nervosa, schizophrenia) are being researched. In existing systems, a lead carrying four ring electrodes at its tip is connected to an implantable pulse generator.

SUMMARY

In general, the disclosure describes techniques, devices, and systems for checking synchronization between two or more implantable modules of an implantable medical device system. A system with two or more distinct modules may provide various functions such as delivery of a therapy to a patient, and the modules may need to be synchronized in order to effectively deliver the therapy. For example, a second module may monitor one or more characteristics of an AC power signal (e.g., count the number of cycles in the AC power signal, which could be cycles in the voltage or current domain) to determine when the first module is expected to output the therapy (e.g., output an electrical stimulation signal). When the output of therapy is not expected, the second module may check to see if in fact therapy is not being output. Absence of therapy indicates synchronization between the first and second modules, whereas the presence of therapy indicates unsynchronization between the first and second modules. The second module may take steps to correct or reestablish synchronization and/or terminate the output of therapy until synchronization can be reestablished.

In one example, the disclosure is directed to a system that includes a first module configured to output a therapy, and a second module distinct from the first module, the second module configured to receive, from the first module, an alternating signal, monitor a characteristic of the alternating signal, determine, based on the characteristic of the alternating signal, a period of time during which the first module is expected to one of output the therapy or refrain from outputting the therapy, and check, during the period of time and based on whether the first module is outputting the therapy, a synchronicity between the first module and the second module.

In another example, the disclosure is directed to a method that includes receiving, by a second module distinct from a first module, an alternating signal, wherein the first module is configured to output a therapy, monitoring, by the second module, a characteristic of the alternating signal, determining, by the second module and based on the characteristic of the alternating signal, a period of time during which the first module is expected to one of output the therapy or refrain from outputting the therapy, and checking, by the second module and during the period of time, a synchronicity between the first module and the second module based on whether the first module is outputting the therapy.

In another example, the disclosure is directed to a system including means for receiving an alternating signal at the second module distinct from the first module, wherein the first module is configured to output a therapy, means for monitoring a characteristic of the alternating signal, means for determining, based on the characteristic of the alternating signal, a period of time during which the first module is expected to one of output the therapy or refrain from outputting the therapy, and means for checking, during the period of time and based on whether the first module is outputting the therapy, a synchronicity between the first module and the second module.

In another example, the disclosure is directed to a computer-readable medium storing instructions that, when executed by one or more processors of a second module, cause the one or more processors to receive, from a first module distinct from the second module, an alternating signal, wherein the first module is configured to output a therapy, monitor a characteristic of the alternating signal, determine, based on the characteristic of the alternating signal, a period of time during which the first module is expected to one of output the therapy or refrain from outputting the therapy, and check, during the period of time and based on whether the first module is outputting the therapy, a synchronicity between the first module and the second module.

The details of one or more examples are set forth in the accompanying drawings and the description below. Other features, objects, and advantages of the disclosure will be apparent from the description and drawings, and from the claims.

DETAILED DESCRIPTION

Figure 1:
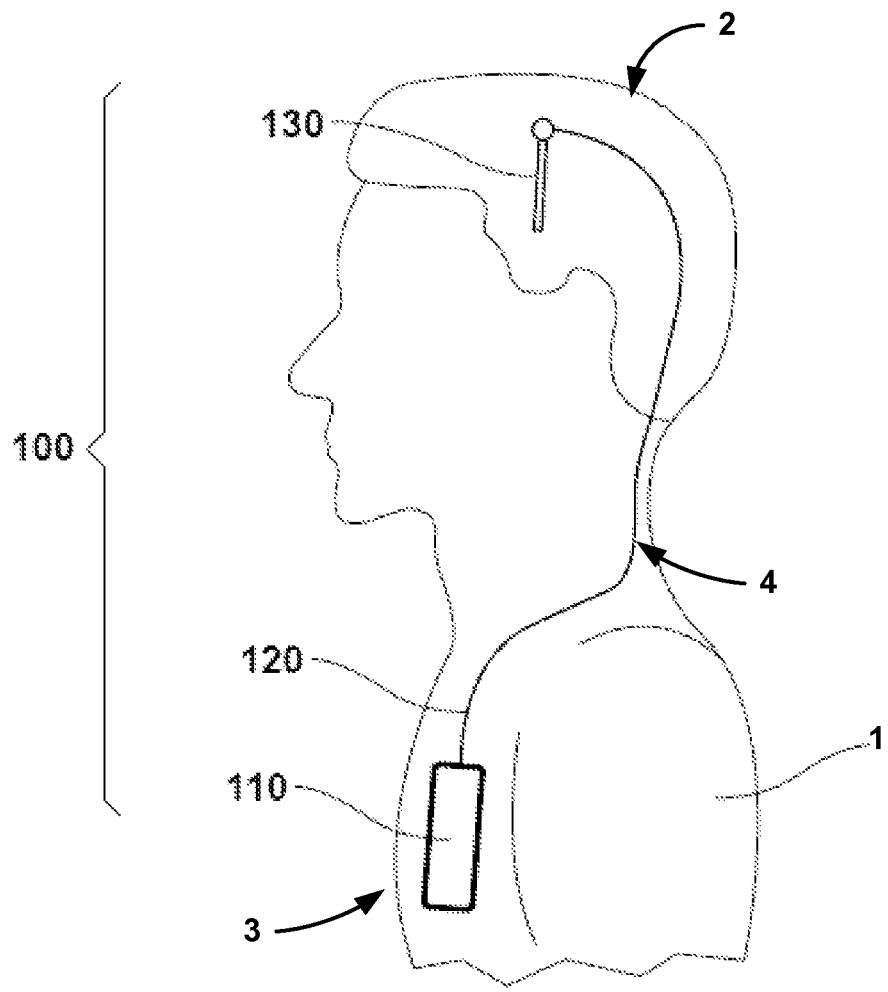
FIG. 1 a conceptual drawing of an example neurostimulation system that delivers deep brain stimulation (DBS) according to the present disclosure.

As described herein, systems, devices, and techniques may include maintaining, checking, and/or correcting synchronization between two or more modules of a system. Generally, a DBS lead may include a plurality of ring electrodes, e.g. four 1.5 mm-wide cylindrical electrodes at the distal end spaced by 0.5 millimeters (mm) or 1.5 mm. In one example, the diameter of the lead may be 1.27 mm and the metal used for the electrodes and the interconnect wires may be an alloy of platinum and iridium. The coiled interconnect wires coupled to respective electrodes may be insulated individually by a fluoropolymer coating and protected in a urethane tubing having a thickness of a few tens of microns. With this type of electrode and lead design, the electrical current distribution emanates uniformly around the circumference of the cylindrical electrodes, which typically results in stimulation of all areas surrounding the electrode.

Some neurostimulation and/or neurorecording systems may include a greater number of smaller electrodes than traditional systems using a technology based on thin film manufacturing. Examples include a lead made from a thin film based on thin film technology, as e.g. described in WO 2010/055453 A1, and the entire content of WO 2010/055453 A1 is incorporated by reference herein. In some examples, a thin film may carry multiple electrodes to cover the distal tip of the thin film with an array of electrodes, and the thin film may be assembled into a lead. Such leads having an array of electrodes may enhance the precision available to a system to address the appropriate target in the brain and relax the required accuracy of positioning the lead during implantation in the patient. Meanwhile, the electrode array may reduce undesirable side effects due to avoiding undesired stimulation of neighboring areas to target areas. Example leads that are based on thin film manufacturing are, for example, described by U.S. Pat. No. 7,941,202 and have been used in research products in animal studies. The entire content of U.S. Pat. No. 7,941,202 is incorporated by reference herein.

In some examples, the lack of fine spatial control over current and electric field distributions in cylindrical electrodes results in stimulation that can spread into adjacent structures that are not intended to receive electrical current and result in side-effects in as much as 30% of patients. To overcome this lack of spatial control, however, systems with high density electrode arrays (e.g., systems with leads constructed of electrodes carried on a thin film) can be used for providing the ability to steer the stimulation field to the appropriate intended target structures instead of unintended structures (hence the term "steering brain stimulation"). The clinical benefit of DBS may be largely dependent on the spatial distribution of the stimulation field in relation to brain anatomy. To improve therapeutic benefits while reducing unwanted side-effects, a DBS system may include stimulation field steering via an electrode array to provide precise control over the stimulation field.

During stimulation with DBS leads, electrodes may be configured to provide monopolar, bipolar, or even multipolar electrical stimulation. Neurostimulator devices with steering brain stimulation capabilities may have a large number of electrode contacts (e.g., an electrode array with more than ten electrodes) that can be connected to electrical circuits such as current sources and/or a system ground. In one example, electrical stimulation may be considered monopolar when the distance between at least one anode and at least one cathode is several times larger than the distance of the cathode to the stimulation target. During monopolar stimulation in homogeneous tissue, the electrical field is distributed roughly spherical, similar to the field from a point source. When the anode is located more closely to the cathode, the distribution of the electrical field becomes more directed in the anode-cathode direction. As a result of the closely located anode and cathode, the electrical field may become stronger and neurons are more likely to be activated in this area due to a higher field gradient between the electrodes.

Although the exact mechanisms of DBS are unknown, it is hypothesized that polarization (depolarization and/or hyperpolarization) of neural tissue is likely to play a role both for suppression of clinical symptoms and for induction of stimulation-induced side-effects. In order to activate a neuron it has to be depolarized. In some cases, neurons are depolarized more easily close to the cathode than by the anode (e.g., about 3-7 times more depending on type of neuron or other characteristics in some examples).

In an effort to design minimally invasive systems, such as DBS systems or other types of systems for neurostimulation and/or neurorecording or systems that deliver other types of therapy to a patient, components of these systems may be separated into several, and typically smaller, implantable electronic modules. In other words, several modules may be configured and constructed to perform the same functions as a single device, but the several modules may provide for lower profiles and/or different shapes for the system when implanted or allow for the modules to be implanted in different locations that would not be possible with a single larger device. Multiple modules may also provide improved functions (e.g., improved telemetry signals or heat dispersion) of a device due to various modules being optimally placed within the patient. In another example, multiple implantable modules may facilitate implantation for leads with many electrodes such that a physician can implant a module pre-attached to one or more leads with respective electrical connections instead of physically attaching the leads and making the required electrical connections during surgery. However, a system with multiple modules may require that the electronics of the different modules of the system are synchronized to operate since some functions of the operation may be distributed between the different modules. In one example, synchronization between modules may allow for cross-point switches of a switch matrix in one module to be turned off in in order to be refreshed or recharged (e.g., when a second module is not delivering a stimulation signal to the switch matrix). Although synchronization may not be required in some examples, synchronization between modules may still provide more optimal functionality than could be achieved without synchronization between the different modules.

A first possible approach to synchronize the electronics of the different modules may to send synchronization data-packet at the same frequency as the electrical stimulation pulses via the available communication interfaces of the electronic modules. This data-packet approach for synchronization may require an overhead for communication (e.g., data bandwidth) and increased power consumption and may thus be undesirable.

A second possible approach to synchronize the electronics of the different modules is to send synchronization data-packets at a lower frequency than the electrical stimulation pulse rate but at a frequency locked to the stimulation pulse rate (e.g., the data packets may be sent at an integer multiplier of the stimulation pulse rate). However, this approach requires a power-consuming recovery circuit in the second electronic module (which is synchronized to, and receives the data-packets from, the first module). The recovery circuit may be used to generate a timing signal at the electrical stimulation frequency rate. Similarly, the second module could start a timer (e.g., using an oscillator of the second module) upon receiving a data-packet from the first module. The first module could frequently send the data-packet to restart timing to limit the possible error in timing by using an oscillator different from the clock of the first module. In other words, the second module could start and restart the timer whenever a new data-packet (e.g., a packet indicating the start to another round of stimulation pulses) is received from the first module.

A third possible approach to synchronize the electronics of the different modules may to use the stimulation pulse generator (e.g., the generator that may be housed by the first module such as an implantable pulse generator or IPG) itself to generate synchronization pulses transmittable to another module, but this approach is also very power inefficient and requires complex hardware. Increased power consumption will reduce the battery lifetime of the system (e.g., the battery lifetime of an implantable pulse generator) that may require explantation and replacement of the battery or the module carrying the battery to extend the useful life of the system.

As described herein, the techniques and systems of the present disclosure may improve a system for therapy and/or monitoring (e.g., neurostimulation and/or neurorecording) with a method and means for synchronizing different electronic modules of a system, such as a system for neurostimulation and/or neurorecording. For example, the system may provide for very efficient and effective synchronization of different electronic modules of the system.

In one example, a system includes a first module configured to output a therapy (e.g., a module that includes a pulse generator) and a second module (e.g., a module that includes a switch matrix for coupling stimulation signals to appropriate electrodes, where the switches of the switch matrix benefit from synchronized activity between first and second modules) distinct from the first module. In some examples, the first module may also include the AC power source that generates an AC power signal. The second module may receive the AC power signal and monitor a characteristic (e.g., count a number of cycles) of the AC power signal. These characteristics may be sensed in the power, voltage, or current domain. In addition, the second module may determine, based on the characteristic of the AC power signal, a period of time during which the first module is expected to refrain from outputting the therapy. For example, the second module may receive instructions from the first module indicating pulse durations (e.g., as a number of AC power signal cycles) for different electrode combinations such that the second module can use the switch matrix to select the appropriate electrode combinations at the appropriate times. The second module may also check, during the period of time during which no therapy should be output from the first module, a synchronicity between the first module and the second module. If the second module detects output of therapy during this period of time, the second module may initiate correction of the unsynchronization between the first and second module. For example, the second module may raise a flag in a status register indicating that the second module is no longer synchronized with the first module. The second module may turn off the switch matrix and/or take other actions that prevent possible erroneous therapy delivery. Consequently, the first module may identify that the second module is no longer synchronized when the first module determines that it cannot output stimulation pulses or when the first module reads the status register and identifies the synchronization error flag. Upon determining that the modules are not synchronized, the first module may stop stimulation therapy, restart the second module, and re-initiate stimulation.

In another example, the synchronization of the different modules of the system may include at least one AC power source configured to generate an AC power signal, at least a first electronics module (e.g., a first module that includes electronics) and at least a second electronics module (e.g., a second module that includes electronics) and at least one synchronizing means adapted to synchronize the first and the second electronics modules, wherein the synchronizing means uses the AC power signal for synchronization. In other words, one example of the present disclosure is to utilize an already existing signal in the system (e.g., the power signal) for synchronization between different modules. In this manner, the system may be able to avoid the generation and/or transmission of additional signals that require extra power.

One potential advantage of using the AC power signal for monitoring when stimulation signals should and should not be output by the first module is to achieve a very power-efficient, robust, and reliable synchronization process for the system, e.g., to synchronize the several modules of a system for neurostimulation and/or neurorecording. The system may not need to utilize the communication bandwidth between modules to check and/or achieve synchronization or provide additional circuitry to monitor other signals. Instead, the system may utilize an already necessary power signal to monitor synchronization between modules of the system. Thus, the problem of failed synchronicity between modules of the system can be elegantly and reliably detected with relatively small power overhead requirements. Although the power signal may be used as a clock signal for counting pulses, the second module may still receive another type of signal (e.g., a start pulse from a pulse generator of the first module) and/or monitor another type of signal (e.g., signals from a pulse generator) in order to determine if the two modules are still synchronized.

In one example, the implantable pulse generator (IPG) that generates the stimulation pulses may be the first electronics module, and the active lead can (ALC) for addressing the electrodes (e.g., operating a switch matrix connecting stimulation signal lines and electrodes) carried by the stimulation lead of the system may be the second electronics module of the system. By way of the synchronizing means, which may use the AC power signal for synchronization, the IPG and the ALC can be synchronized for effectively delivering stimulation signals generated by the IPG (e.g., the first module) through electrode combinations selected by the ALC (e.g., the second module). For example, the switch matrix of the second module may include cross-point switches that recharge between delivery of stimulation pulses (e.g., each switch may have a local supply voltage implemented through a capacitor from which current is supplied when controlling the state of the switch. In addition, the capacitor can be discharged through unavoidable (parasitic) leakage currents). This example switch matrix is further discussed in, for example, U.S. Patent Application Publication No. 2015/0091533, entitled "CONTROL CIRCUITRY AND METHOD FOR CONTROLLING A BI- DIRECTIONAL SWITCH SYSTEM, A BI-DIRECTIONAL SWITCH, A SWITCHING MATRIX AND A MEDICAL STIMULATOR" and filed Dec. 10, 2014, the entire content of which is incorporated by reference. In other words, the switches may need to be open, or non-conducting, in order to recharge. However, in order for the switches to be open, the pulse generators should not be attempting to deliver stimulation pulses. Therefore, the non-stimulation period between pulses should be known by the second module in order to open the switches during this non-stimulation period of time. The second module may monitor synchronicity with the first module in order to accurately time the non-stimulation period that may be needed to recharge the switches of the switch matrix.

Generally, an AC power signal is described herein as an example signal from which the second module can detect and count cycles in order to maintain and check synchronicity between the first and second modules. In other words, the AC power signal may be used to provide power and provide a clock signal. However, any alternating signal (i.e., a signal that includes cycles) that provides functionality may be used in other examples. In other examples, the alternating signal may be used solely for synchronization purposes in addition to checking for the presence of other signals to determine synchronization. For example, an alternating signal (e.g., an AC signal) used to provide a communication function or an AC clock signal not used to provide power may be used to provide the clock function. In other examples, the alternating signal may not be an electrical signal. For example, an alternating pressure signal, such as cyclical pressure waves caused by a pump that delivers a therapeutic fluid from the first module, may be used to provide the cycles detected by a pressure or flow sensor, for example, of the second module. In this manner, the second module may count the cycles from any alternating signal that provides a first function (e.g., operating power from an AC power signal) in order to check the synchronicity of the first and second modules, where checking the synchronicity is the second function different from the first function.

FIG. 1 a conceptual drawing of an example neurostimulation system 100 that delivers deep brain stimulation (DBS) according to the present disclosure. In other examples, neurostimulation system 100 may be directed to other applications such as spinal cord stimulation or pelvic floor stimulation. Neurostimulation system 100 comprises at least a controller 110 (e.g., a first module comprising one or more pulse generators) that may be surgically implanted in the chest region 3 of a patient 1, typically below the clavicle or in the abdominal region of a patient 1. Controller 110 can be configured to supply the necessary current or voltage pulses (e.g., an electrical stimulation signal) to lead arrangement 130. Lead arrangement 130 may include one or more modules distinct from controller 110. DBS system 100 may further include a connecting cable 120 (e.g., an extension wire) connected to the controller 110 and running subcutaneously to the skull 2, such as along the neck 4, where it terminates in a connector.

DBS lead arrangement 130 may be implanted in the brain tissue, e.g., through a burr-hole in the skull. DBS lead arrangement 130 may include one or more leads coupled to at least one module including a switch matrix (which may be housed within a second module). In addition, DBS system 100 may include one or more grounding electrodes in addition to electrodes carried in lead arrangement 130. Although system 100 is described for neurostimulation and/or neurorecording, system 100 may alternatively delivery different types of therapy (e.g., drug therapy or fluid delivery) or record different types of physiological characteristics (e.g., motion of patient, temperature, pressure, chemistry, etc.).

The neurostimulation and/or neurorecording system of system 100 may be a deep brain stimulation (DBS) system. Such a system may include a plurality of electrodes (e.g., greater than ten electrodes such as 20, 32, 40, 64 or 128 electrodes). To address or configure each of the electrodes, such as to set them active or inactive or reduce or increase the stimulation current provided by the electrode, control electronics may be provided in the second electronics module, for example, the active lead can. These control electronics may include features such as a switch matrix to address each electrode of the plurality of electrodes and to distribute the stimulation current from controller 110 accordingly. Thus, the second module that includes the switch matrix may require synchronization in order to appropriately switch stimulation signals across the appropriate electrodes that should deliver the stimulation signals to the patient 1. For example, the second module may recharge the switches of the switch matrix during non-stimulation periods to maintain operation of the switches. In some examples, synchronization may also allow the second module to select different sets of electrodes using the switches for different stimulation pulses delivered over time.

The lead of system 130 may include at least 20 electrodes, e.g., approx. 30 to 45 electrodes, more specifically approximately 40 electrodes in one example or up to 128 electrodes in other examples. Each lead may include more than 128 electrodes in other examples. This number of electrodes may facilitate the creation of one or more stimulation fields selected to conform to a target region of tissue and which may form a three-dimensional field adapted to the target tissue or region. In this manner, only those tissue regions that are intended to be stimulated may be affected by the stimulation field provided by the plurality of electrodes.

In some examples, the electrodes may form a complex electrode array configured to create a stimulation field that is adapted to and conforms with the target region. The complex electrode array generally refers to an arrangement of electrodes at multiple non-planar or non-coaxial positions, in contrast to simple electrode array geometries in which the electrodes share a common plane or common axis (e.g., a plurality of ring electrodes stacked in one dimension). In this manner, electrodes of the complex electrode array may be disposed at different radial, circumferential, and/or axial positions of a lead.

An example of a simple electrode array geometry is an array of ring electrodes distributed at different axial positions along the length of the lead. An example of a complex electrode array geometry, in accordance with this disclosure, is an array of electrodes positioned at different axial positions along the length of the lead, as well as at different angular (or radial) positions about the circumference of the lead. These configurations may apply to cylindrically shaped leads and leads having other shapes such as triangles, squares, or other polygon or non-uniform shapes.

An AC power supply may generate an AC power signal. The AC power supply may be housed within controller 110 or another module of system 100. The AC power signal may be used as clock signal. The AC power signal may be kept at a known frequency and thus a periodic AC power signal can be used as clock signal for synchronization of the at least some modules of system 100. In some examples, the AC power signal may change in frequency, but as long as the change in frequency is coordinated between the first and second modules, the change in frequency is possible. In other examples, presence of the AC power signal may allow the second module to perform a function, and when the first module 110 removes the AC power signal, the second module is switched off. This periodic availability of the AC power signal may be used to synchronize both modules. In this manner, information, such as clock information, needed for synchronization can be derived from the AC power signal (e.g., counting cycles/pulses of the AC power signal). In some examples, the AC power signal may be locked to a frequency of the stimulation frequency for neurostimulation. In this manner, the AC power signal may advantageously contain information about the stimulation frequency, which may be an important factor and information used for synchronization. For example, the AC power signal may have a frequency that is an integer multiple of the stimulation frequency. In other words, the second module may know that a stimulation pulse is delivered every 20 cycles of the AC power signal, for example.

The means for synchronizing different modules (e.g., a processor, controller, integrated circuit, or other circuitry) may be adapted to count the AC power signal pulses or AC power signal cycles. Counting pulses or cycles may be a very advantageous and power efficient way of synchronizing different modules together. The synchronizing means may be adapted to check if the synchronicity is still present by sensing at least one pulse generator line for stimulation in a period of time during which no stimulation current should be present. In this manner, checking for synchronization may be achieved with analysis of the (absence of) stimulation signal in an efficient process. In one example, the second module may monitor the pulse generator lines with a current detector (which may be by way of a current-to-voltage converter such as a resistor in order to indirectly detect current or directly measure voltage) and generate a synchronization error flag if current is present when it is not expected by the second module.

In general, two or more modules may require synchronization to perform a certain task correctly or advantageously. If the modules are not synchronized, an error can occur, efficacy of a function may be reduced, or any other undesirable event could occur. To prevent prolonged synchronization problems, one or more of the modules can check to determine if the modules are synchronized. If one of the modules determines that synchronization no longer is in place, one or more modules may perform follow-up actions. These follow-up actions may include stopping a function, restarting a module, or otherwise re-establishing synchronization between the modules before continuing to perform one or more functions.

In some examples, the synchronizing means (e.g., the first module or controller of the AC power supply) may be adapted to add a marker to the AC power signal. The inclusion of a marker signal may simplify the synchronization by the marking indicating the start (e.g., a start pulse) and/or stop of outputting therapy such as a stimulation signal. In this manner, the synchronizing means may be adapted to add a start marker and an end marker to the AC power signal for marking a stimulation current sensing phase. The second module may more easily identify the on and off phases of stimulation. The synchronizing means, such as the second module, may be adapted to detect the marker added to the AC power signal for monitoring the synchronization. Upon the detection of the marker, the second module may trigger the start or stop of synchronization checking, respectively. In some examples, the second module may start an internal timer based on the marker in the AC power supply instead of counting cycles of the AC power signal.

In other examples, the synchronizing means may be configured to generate a clock pulse flip marker and use the clock pulse flip marker for synchronization. By flipping a part of the AC power signal (e.g., inverting a portion of the power cycle), the synchronizing means can add a highly recognizable marker to the AC power signal. In addition, the power consumption may not be negatively affected by creating the clock pulse flip marker (particularly when the power transfer takes place at the rising and falling edges of the power source signal and the number of edges per period, such as a stimulation period, remains the same). Alternatively, or additionally, the synchronizing means may be configured to use blanking of at least a part of a pulse of the AC power signal for synchronization. By blanking of at least a part of the pulse of the AC power signal, the synchronizing means can add a highly recognizable marker to the AC power signal without increasing the power consumption.

In some examples, the synchronizing means may be adapted to change a characteristic of the AC power signal, such as the frequency of the AC power signal, for synchronization. Such a frequency change of the AC power signal is also a well-recognizable marker added to the AC power signal that would be detectable by another module.

Furthermore, the present disclosure describes a method for synchronizing electronic modules of a system for neurostimulation and/or neurorecording. Accordingly, an AC power signal may be used for power transmission between the electronic modules (e.g., from the AC power source in one module to one or more other modules) and the electronic modules are synchronized by using the AC power signal directly or indirectly. All above structural features and functional features of the system of the present disclosure as disclosed above may be used alone or in combination in connection with the method according to the present disclosure.

Figure 2A:
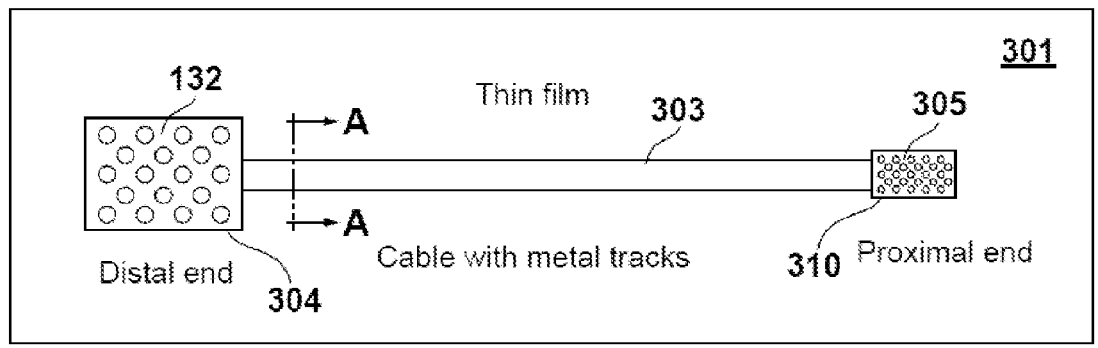
FIGS. 2A, 2B, and 2C are schematic diagrams of an example thin film, lead, and probe of a neurostimulation system for DBS.
Figure 2B:
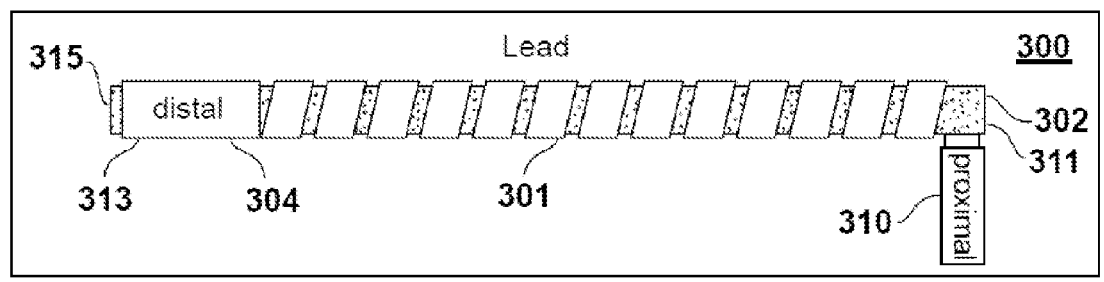
Figure 2C:
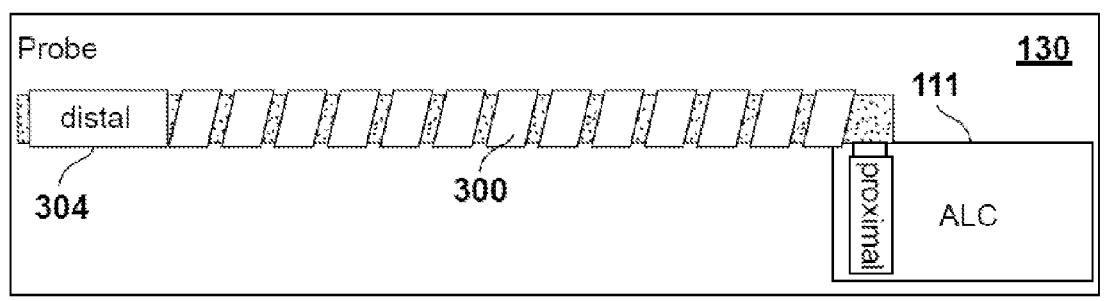

FIGS. 2A, 2B, and 2C are schematic diagrams of an example thin film, lead, and probe of a neurostimulation system for DBS. For example, FIG. 2A illustrates an example, thin film 301, FIG. 2B illustrates an example DBS lead 300, and FIG. 2C illustrates an example Deep Brain Stimulation probe 130 that include DBS lead 300 and a second module 111 (e.g., an active lead can). Second module 111 may include electronic means to address electrodes 132 (e.g., switch current or ground lines across each electrode) disposed on the distal end 304 of the thin film 301. Electrodes 132 may be arranged at the distal end 313 of lead 300 and next to the distal tip 315 of the DBS lead 300.

Lead 300 may include a carrier 302 for thin film 301. Carrier 302 may be sized and shaped to providing the mechanical configuration of DBS lead 300 and the thin film 301. In other words, thin film 301 may be wrapped around the circumference or diameter of carrier 302. Thin film 301 may include at least one electrically conductive layer and may be constructed of a biocompatible material. The thin film 301 may be assembled to carrier 302 and further processed to constitute lead 300.

The thin film 301 for a lead may be formed by a thin film product having a distal end 304, a cable 303 with metal tracks, and a proximal end 310. Proximal end 310 of the thin film 301 may be arranged at the proximal end 311 of lead 300 and is electrically connected to the second module 111. The second module 111 may include the switch matrix of the DBS steering electronics that selects configurations of electrodes 132. The distal end 304 comprises electrodes 132 for brain stimulation, for example. Proximal end 310 of thin film 301 includes interconnect contacts 305 for each metal track or line in the cable 303. The cable 303 comprises metal tracks or lines (not shown) to electrically connect each of distal electrodes 132 to a respective and designated proximal interconnect contact 305. In other examples, lead 300 may be constructed using other techniques and materials such as coiled conductors running the length of lead 300 to couple respective electrodes to module 111.

Figure 3:
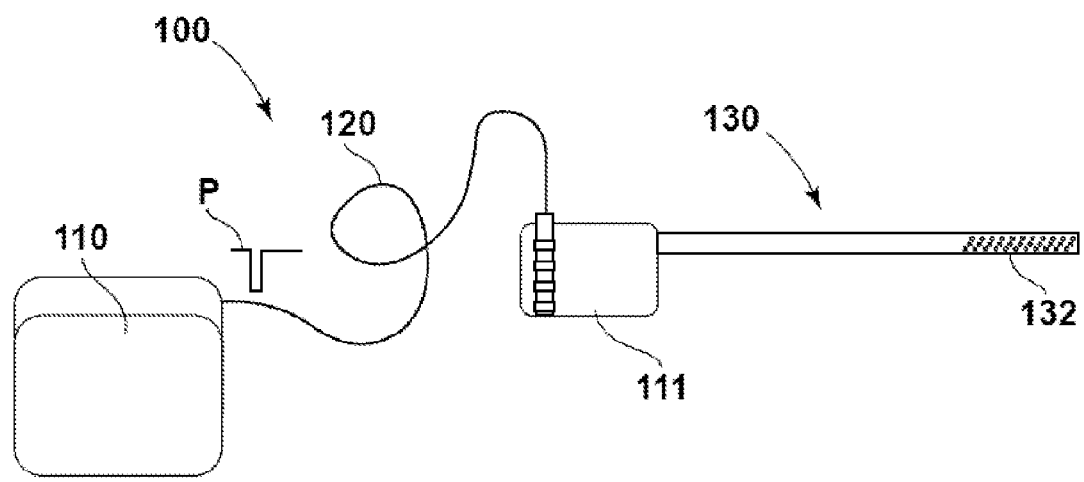
FIG. 3 is a conceptual drawing of an example system that delivers DBS.

Second module 111 may include a switch matrix, or multiplexer, that is used to couple, or decouple, each electrode of electrodes 132 to one or more pulse generator lines and ground provided to second module 111 via a connecting cable (e.g. connecting cable 120 of FIG. 3). In other words, second module 111 may use the switch matrix to switch stimulation signal lines and a ground line across each of the electrodes 132. In some examples, second module 111 may include other control electronics, such as a microprocessor or other integrated circuitry, resistors, and capacitors.

FIG. 3 is a conceptual drawing of an example system 100 that delivers DBS. System 100 is described for brain applications, such as neurostimulation and/or neurorecording as a deep brain stimulation system 100 as shown in FIG. 1. The probe system 100 may include at least one probe 130 for brain applications with stimulation and/or recording electrodes 132. In one example, forty electrodes 132 can be provided on the outer body surface at the distal end of the probe 130. Controller 110 (e.g., a first module) may include one or more pulse generators that generator and supply pulses P to a second module 111 (e.g., an active lead can) by means of the connecting cable 120. In some examples, the controller 110 can be or include an implantable pulse generator. In other examples, controller 110 may be configured to simultaneously couple to two or more different second modules 111 and respective probes 130 via one or more connecting cables 120. In other examples, system 100 may include additional distinct modules that provide additional functionality and/or additional modules that split the functionality provided by modules 110 and 111.

As described herein, system 100 may include first module 110 includes one or more stimulation pulse generators. First module 100 may also include components such as a power supply, one or more processors, a memory, a communication unit for transmitting and/or receiving information from an external device, and other components. Second module 111 may include a switch matrix and, in some examples, one or more processors, a memory, and connectors for coupling lead 300 and connecting cable 120. Second module 111 may have a housing encompassing the control electronics such as the switch matrix. In some examples, the housing may be electrically nonconductive such as an epoxy or polymer that insulates and protects the components of second module 111. The electrically nonconductive material may reduce conductivity of the housing and/or insulate the brain from any interference caused by the components of second module 111.

Connecting cable 120 may connect first module 110 to second module 111. The plurality of electrodes 132 are disposed distal of second module 111 and on lead 300 of probe 130. The control electronics for the plurality of electrodes may provide at least one of neurostimulation and/or neurorecording via at least one electrode of the plurality of electrodes 132; it may also ground at least one electrode of the plurality of electrodes 132. The control electronics are arranged in at least the first module 110 and the second module 111, but one or more additional modules may also include at least some of the control electronics. As described in FIG. 2A, probe 130 may include lead 300 constructed of a thin film 301 carrying the plurality of electrodes 132. Lead 300 may be electrically coupled to the switch matrix of second module 111.

Figure 4:
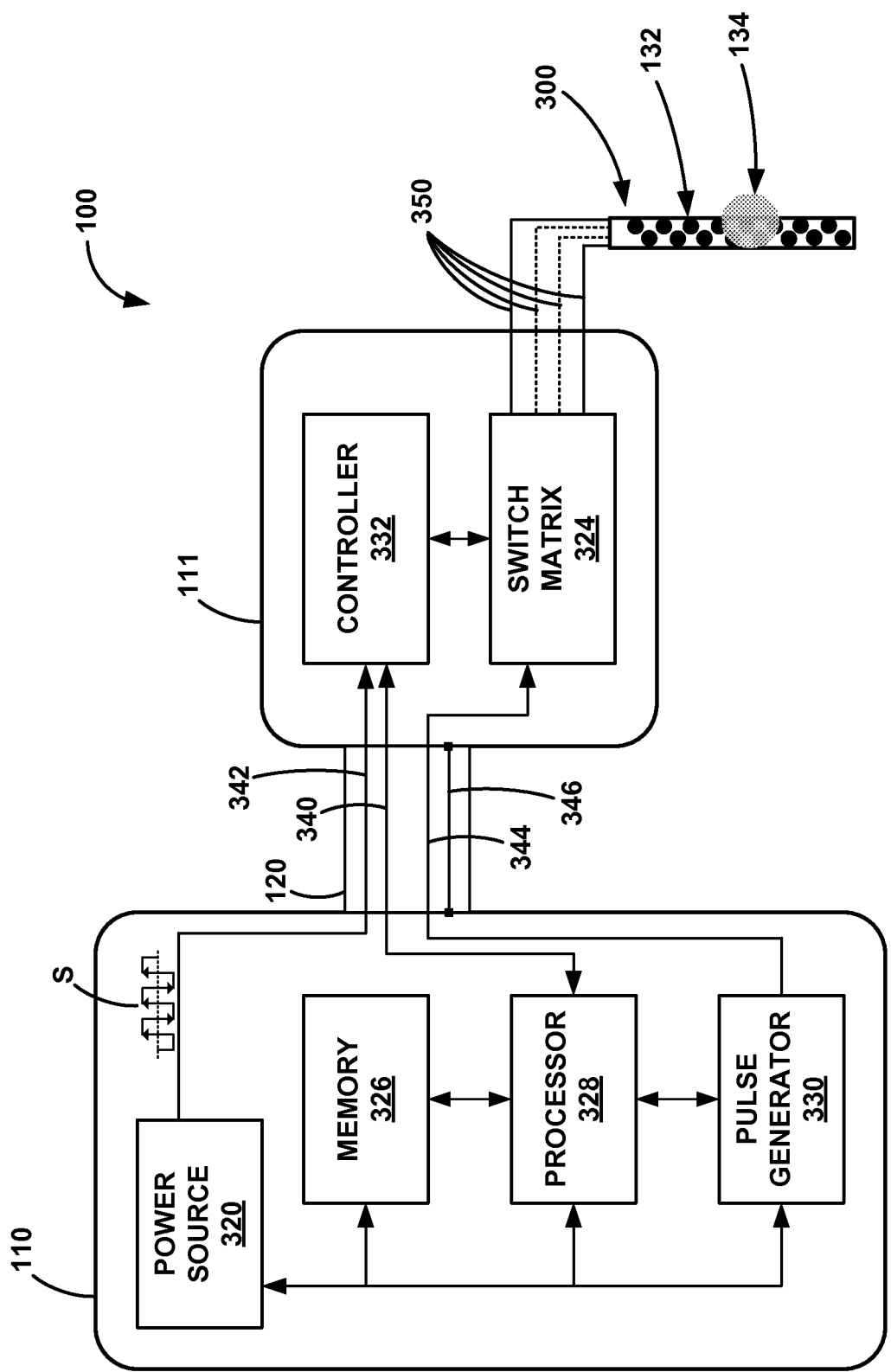
FIG. 4 is a schematic diagram of an example DBS system that includes a first module in communication with a second module.

FIG. 4 is a schematic diagram of an example DBS system 100 that includes a first module 110 in communication with a second module 111. System 100 may be configured for neurostimulation and/or neurorecording. As shown in FIG. 4, system 100 is a modular system and includes first module 110 (e.g., an IPG), second module 111, lead 300, and connecting cable 120 that connects first module 110 and second module 111. First module 110 may include AC power source 320, memory 326, processor 328, and pulse generator 330. Second module 111 may include controller 332 and switch matrix 324. Lead 300 may include electrodes 132 for delivering stimulation signal 134. In some examples, first module 110 and/or second module 111 may include a communication module configured to transmit and/or receive data with other devices or systems (e.g., receive stimulation programs and/or transmit obtained data from patient 1).

First module 110 may transmit several signals to second module 111 via connecting cable 120. For example, first module 110 may provide a pulse generator output (PG1), a data channel (DATA IN/OUT), a combined power and clock line (PWR/CLK), and a connection for battery ground (BATTERY GND) which are all connected to second module 111, i.e. the second electronics module or active lead can. Second module 111 is connected to lead 300 having 64 electrodes 132, as one example. In some examples, lead 300 may carry fewer electrodes 132, e.g. 40 electrodes, or more electrodes, e.g. up to or more than 128 electrodes.

System 100 includes at least one AC power source 320 configured to generate an AC power signal S. Although first module 110 may house AC power source 320 as shown in FIG. 4, AC power source 320 may be housed in a different module in other examples. The power (PWR) and clock (CLK) line 342 may be used to transmit a power and clock signal from first module 110 to second module 111. The power and clock signal can be a bipolar square wave voltage S, generally described as the AC power signal generated by AC power source 320. In this manner, line 342 may carry the AC power signal from AC power source 320 to controller 332 of second module 111 such that second module 111 may also include power management circuitry that rectifies the AC power signal and distributes the power to electrical components of second module 111. The clock signal from the AC power signal may be obtained by controller 332 prior to rectification. AC power source 320 may include a rechargeable or non-rechargeable battery or a direct access to another power supply.

The DATA IN/OUT line 340 is used for communication between first module 110 and second module 111, including data communication to program the electronics (e.g., controller 332) in second module 111 to connect the selected electrodes of electrodes 132 to the appropriate output from pulse generator 330 via line 344 or the ground of AC power source 320 via line 346. Line 346 is shown in FIG. 4 representing system ground for the electrical components of each of modules 110 and 111. In this manner, processor 328 may program controller 332 by sending data signals over line 340 (e.g., a communication line) to controller 332 such that controller 332 can operate switch matrix 324 for selecting the appropriate electrodes and for field steering of the stimulation signal from first module 110. In addition, the DATA IN/OUT line 340 can be used to transmit recorded data obtained during neurorecording from second module 111 to first module 110. Pulse generator 330 may generate stimulation signals at the control of processor 328 and transmit the stimulation signals to switch matrix 324 over line 344. Although only one pulse generator 330 and one line 344 are described as generating and transmitting a single stimulation signal, two or more pulse generators and respective lines may be used in other systems to provide two or more independent stimulation signals to second module 111.

Connecting cable 120 may include conductors for each of lines 340, 342, 344, and 346. Each of the conductors may be electrically coupled to respective contacts at the proximal and distal end of connecting cable 120. Each of the contacts of connecting cable 120 may be configured to electrically mate with respective contacts of first module 110 and second module 111. In this manner, each of lines 340, 342, 344, and 346 may include a conductive path over one or more conductive elements in order to couple the various components of first module 110 and second module 111. In some examples, lines 340, 342, 344, and 346 may be split into two or more different connecting cables.

Controller 332 may be configured to operate switch matrix 324 based on data received from processor 328. Switch matrix 324 may include a plurality of switches operable by controller 332 to switch stimulation signals from pulse generator 330 and ground to AC power source 320 across each electrode of electrodes 132. In one example, the switch matrix 324 may include cross-point switches that allow stimulation signals from one or more pulse generators to be applied to respective electrodes of electrodes 132. In this manner, controller 332 may be configured to select various electrode configurations in order to achieve field steering of stimulation signal 134. Switch matrix 324 may be configured to switch between two or more stimulation signal lines 344 in other examples. Each electrode of electrodes 132 may be coupled to switch matrix 342 via respective conductors 350, which may be respective metal tracks in the example of a thin film based lead 300. In this manner, controller 332 may selectively couple each electrode to one or more lines incoming from first module 110 such as ground line 346 or stimulation signal line 344.

In general, first module 110 and second module 111 may comprise any suitable arrangement of hardware, alone or in combination with software and/or firmware, to perform the techniques attributed to first module 110, second module 111, and system 100 described herein. In various examples, processor 328 and/or controller 332 may be a processor or include one or more processors, such as one or more microprocessors, digital signal processors (DSPs), application specific integrated circuits (ASICs), field programmable gate arrays (FPGAs), or any other equivalent integrated or discrete logic circuitry, as well as any combinations of such components. Memory 326 may be, for example, as random access memory (RAM), read only memory (ROM), programmable read only memory (PROM), erasable programmable read only memory (EPROM), electronically erasable programmable read only memory (EEPROM), flash memory, comprising executable instructions for causing the one or more processors to perform the actions attributed to them.

Processor 328 may receive operating instructions stored in memory 326. Moreover, although processor 328 and memory 326 are described as separate modules, in some examples, processor 328 and memory 326 (or more components of first module 110 or second module 111) are functionally integrated. Controller 332 may integrate one or more memories (e.g., a memory similar to memory 326) that stores operational instructions for controller 332 and/or data obtained from electrodes 132 and/or data related to the operational status of second module 111. In other examples, second module 111 may include one or more separate memories.

Both the cans (i.e., housings or casings) of first module 110 and second module 111 are typically hermetically sealed and can be made of a conductive material. In some examples, second module 111 may be constructed of an electrically insulative material instead of a conductive material.

As described above, second module 111 may include a switch matrix 324 for connecting the plurality of electrodes 132 to signals received from first module 110, such as the PG1 stimulation signal line 344 or the ground line 346. However, controller 332 may need to be synchronized with the output of stimulation signals from pulse generator 330 such that the intended one or more electrodes of electrodes 132 are coupled to line 344 to receive the appropriate stimulation signal. In some examples, synchronization between first module 110 and second module 111 may allow for the cross-point switches of switch matrix 324 in second module 111 to be turned off in in order to be refreshed or recharged (e.g., when the cross-point switches are open, i.e., not closed, and cannot be used to provide stimulation signals to respective electrodes coupled via the respective cross-point switch). Since pulse generator 330 may periodically change the stimulation signal output on line 344 as needed as part of therapy, the stimulation signal needs to reach the appropriate electrodes. Therefore, a lack of synchronization between the first module 110 and second module 111 could result in the delivery of unintended stimulation fields to anatomical structures, in addition to the inability to properly recharge the switches of the switch matrix.

Therefore, system 100 may include synchronizing means for detecting and, in some examples, correcting synchronization issues between modules such as between first module 110 and second module 111. For example, first module 110 may be configured to output a therapy, such as an electrical stimulation signal or a therapeutic fluid intended to be received by the patient. Second module 111, distinct from first module 110, may be configured to receive the AC power signal from AC power source 320 (e.g., via line 342). Second module 111 may also be configured to monitor a characteristic of the AC power signal, determine, based on the characteristic of the AC power signal, a period of time during which first module 110 is expected to refrain from outputting the therapy, and check, during the period of time, a synchronicity between first module 110 and second module 111. In some examples, a synchronization start pulse may be generated by first module 111 to indicate when second module 111 should begin counting cycles of the AC power signal.

In this manner, system 100 may utilize the AC power signal as the mechanism to maintain synchronization between multiple modules of the system, such as first module 110 and second module 111. In some examples, the AC power signal may be used as a clock signal where the characteristic of the AC power signal is a periodic cycle (e.g., a positive and negative excursions beyond zero). The AC power signal may include a square wave S that can be used inside second module 111 and the switch matrix 324 (e.g., a cross-point switch matrix) as reference clock. The rectified square wave voltage S can serve as the supply voltage for the electronics of second module 111. If the rectified voltage of the power and clock line 342 is too low to supply the electronics directly, voltage boosting can be applied directly after rectification. The AC power signal S may be a consistent, or at least known, frequency and thus the periodical AC power signal S is used as a clock signal for synchronization. Any clock information needed for synchronization can be derived by the controller 332, for example, from the AC power signal S. In other words, the AC power signal may be a periodic signal that provides the alternating current or voltage, wherein the alternating current or voltage cycle is repeatable and periodic.

Second module 111 may thus be configured to count a number of the cycles of the periodic AC power signal and determine, based on the number of cycles that are counted, that an expected output from first module 110 has terminated. Counting cycles may include counting each rising edge, each falling edge, or any other characteristic of a pulse that may be indicative of the periodic nature of the AC power signal. Second module 111 may then begin the period of time (for determining whether a signal is still output from first module 110) in response to determining that the expected output has terminated. For example, second module 111 may expect that output from the first module 110 occurs for twenty cycles of the AC power signal. Second module 111 may receive communications or data from first module 110 over line 340 that defines the output that will be delivered from first module 110 and instructions regarding any actions second module 111 should take and at what times (e.g., which electrodes should be coupled to the stimulation signal output on line 344 at certain times). After second module 111 counts that twenty cycles have occurred, second module 111 may then determine that the period of time to check for remaining stimulation pulses from first module 110 is to start because the output of therapy should have ceased. This process may require a very low level of power to both maintain and monitor synchronization, especially when the monitoring is duty-cycled, for example, the check is only performed once in every 255 stimulation cycles in one example. However, the check may be performed more or less frequently in other examples.

In some examples, and as shown in the example of FIG. 4, the therapy may be an electrical stimulation signal. First module 110 may include stimulation pulse generator 330 that is configured to output the electrical stimulation signal. Although a pulse generator is described, any signal generator may generate signals other than pulses (e.g., continuous signals such as sine waves or triangle waves). When pulse generator 330 delivers electrical stimulation signals, the AC power signal output by AC power source 320 may be locked to the stimulation frequency of the electrical stimulation signal generated by pulse generator 330. For example, AC power signal S may advantageously contain information about the stimulation frequency, which may be beneficial for synchronization. In other words, although the frequencies of the AC power signal and the stimulation signal may or may not be the same, each frequency may be a multiple of each other such that the frequencies are not completely independent.

In other examples, the AC power signal may be modulated to provide information that second module 111 uses to synchronize with first module 110. AC power source 320 may modulate the AC power signal according to instructions from processor 328 and/or pulse generator 330 or another module (e.g., processor 328 or another circuit) may modulate the periodic AC power signal generated by AC power source 320. For example, first module 110 may be configured to add a marker to the AC power signal, where the marker is a change in one or more characteristics of the AC power signal. The characteristic changed or modulated in the AC power signal to include a marker may be at least one of a frequency of the AC power signal (e.g., changing a frequency of the signal or adding or skipping part or all of a cycle), an amplitude of the AC power signal (e.g., increasing or decreasing an amplitude for one or more pulses during the otherwise baseline amplitude), or a cycle duration of the AC power signal (e.g., increasing or decreasing the pulse width of one or more pulses in an otherwise regular train of consistent pulse widths).

The marker may be indicative of at least one of a beginning of the output of the therapy or an end of the output of the therapy (e.g., the start and/or end of output of the therapy may be output with a respective marker on the AC power signal on line 342). In some examples, the start marker may be created with a different characteristic change than the stop marker. Second module 111 may be configured to identify the marker as a change in the characteristic of the AC power signal. In other examples, the marker may include a clock pulse flip marker such that the AC power signal includes flipping the polarity of one or more pulses in an otherwise train of pulses alternating in polarity. In another example, the marker may include a blanking of at least a portion of the AC power signal (e.g., withholding one or more pulses from an otherwise consistently alternating current signal). Other changes to the AC power signal are also contemplated. AC power source 320 may provide a marker, or another circuit or module of first module 110 may modulate the AC power signal generated by AC power source 320.

The second module 111 may determine to check the synchronicity with first module 110 when an output is not expected to be output by first module 110. In addition, second module 111 may only check for synchronicity periodically or with respect to certain actions. For example, second module 111 may follow a schedule for checking synchronicity (e.g., at certain times of the day, after a certain period of time since the last check, and/or after a certain amount of output of therapy from first module 110). In other examples, second module 111 may check synchronicity before or after a relatively long period of therapy delivery. In this manner, second module 111 may or may not check synchronicity every time during which therapy is expected to be delivered or not delivered.

In one example, second module 111 may be configured to sense for output of the therapy by first module 110 to check the synchronicity, where an absence of the output of the therapy during the period of time is indicative of first module 110 and the second module 111 being synchronized. In other words, if second module 111 does not detect therapy output from first module 110 during a period of time in which no therapy was expected, second module 111 can confirm that the modules are synchronized together.

Conversely, a presence of the output of the therapy during the period of time during which output is not expected may be indicative of first module 110 and the second module 111 being unsynchronized. In other words, if second module 111 detects therapy output from first module 110 during the period of time in which no therapy was expected, second module 111 can determine that the modules are not synchronized. Corrective action may be required in this scenario.

In the example of FIG. 4, second module 111 may be configured to check the synchronicity between second module 111 and first module 110 by sensing, during the period of time, for an electrical stimulation current on at least one pulse generator line (e.g., line 344) from first module 110. Second module 111 may include a switch operable by controller 332 that allows controller 332 to selectively sense the electrical current, or voltage, on the pulse generator line 344. The switch may or may not be included within switch matrix 324. Therefore, controller 332 may sample output from pulse generator 330 in order to determine whether or not second module 111 is synchronized with first module 110. Second module 111 may utilize other mechanisms for checking the output from pulse generator 330 in other examples (e.g., controller 332 may continually monitor the current on line 344, but such monitoring may consume more power than periodic coupling to line 344). If the therapy from first module 110 is pumping a therapeutic fluid, checking for synchronization may include sensing for fluid pressure and/or flow from a pump housed in first module 110.

Second module 111 may be configured to determine that second module 111 is unsynchronized with the first module 110. Responsive to the determination that first module 110 is unsynchronized with second module 111, second module 111 may transmit a request to first module 110 to at least one of terminate outputting the therapy or reset the synchronicity of the first and second modules. In this manner, controller 332 may be configured to perform corrective actions when the modules are determined to be unsynchronized. Controller 332 may send a request to terminate therapy to processor 328 to prevent unintended therapy being delivered to the patient. Alternatively, or in addition, controller 332 may transmit a request to processor 328 to reset or restore the synchronization between modules. A reset or restore may include terminating operation of each module and/or transmitting another synchronization start pulse that initiates synchronized operation.

In other examples, processor 328 may take corrective action in response to receiving a signal from controller 332 that second module 111 is no longer synchronized or in response to directly detecting that the second module 111 is no longer synchronized. For example, second module 111 may be configured to determine that second module 111 is unsynchronized with first module 110 and, responsive to determining that second module 111 is unsynchronized, generate an error flag indicative of the unsynchronization. First module 110 may thus be configured to obtain the error flag from second module 111 and, responsive to obtaining the error flag, perform one or more actions that correct the unsynchronized status between the first and second modules. For example, processor 328 of first module 110 may perform the synchronization check on second module 111 by checking for a flag (e.g., a SYNC_OK flag) that indicates second module 111 is still synchronized (i.e., second module 111 may set the flag to indicate whether or not the modules are still synchronized). In response to determining that second module 111 is no longer synchronized, controller 332 may set a flag (e.g., affirmatively indicate that the modules are synchronized and/or not synchronized) in the register that indicates the modules are not synchronized and processor 328 may take corrective action upon detecting the flag. Other corrective actions may include communication signals exchanged between processor 328 and controller 332 to re-synchronize each module. Re-synchronization may include one or both of modules 110 and 111 adjusting operations to match the other module.

Figure 5:
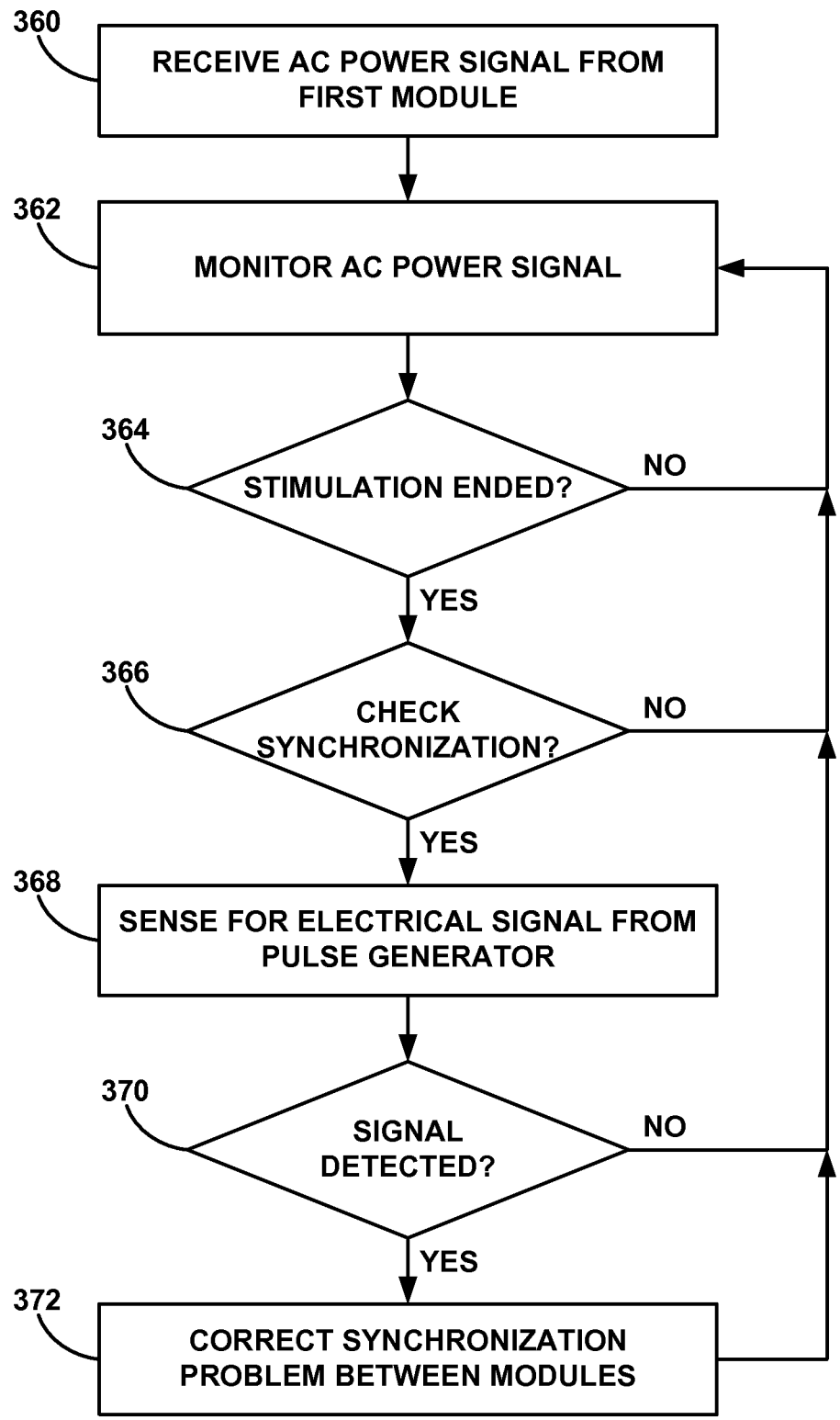
FIG. 5 is a flow diagram of an example process for monitoring the synchronization between two modules of a stimulation system.

FIG. 5 is a flow diagram of an example process for monitoring the synchronization between two modules of stimulation system 100. The example of FIG. 5 is described with respect to controller 332 of second module 111 and processor 328 of first module 110. However, the functions attributed to controller 332 may be performed by other processors or circuits of second module 111 and/or first module 110 in other examples. Moreover, the example process of FIG. 5 may be altered to remove certain steps and/or adding additional steps, such as according to other examples described herein.

As shown in FIG. 5, second module 111 receives an AC power signal from first module 110 (e.g., via AC power supply 320) (360). Controller 332 monitors the AC power signal (e.g., count periodic cycles) to determine when stimulation pulses are delivered and when stimulation pulses will not be delivered (362). These expected periods of stimulation and non-stimulation may be known by counting cycles in the AC power signal from the initial synchronization start pulse that was generated by one or more pulse generators within first module 110. In this manner, controller 332 may monitor the AC power signal when monitoring for synchronization or perform different tasks at different moments in time (e.g. open/close cross-point switches or connect a current detector to the pulse generator lines based on the number of cycles counted from the AC power signal). If electrical stimulation is not expected to have ended ("NO" branch of block 364), controller 332 may continue to monitor the AC power signal (362). If the stimulation output from first module 110 is expected to have ended ("YES" branch of block 364), but controller 332 is not yet scheduled to check for synchronization ("NO" branch of block 366), controller 332 may continue to monitor the AC power signal by counting cycles from the AC power signal (362).

If controller 332 determines that synchronization should be checked ("YES" branch of block 366), controller 332 may sense for any electrical signal (e.g., voltage or current) from pulse generator 330 on pulse generator line 344 because no stimulation pulses are expected at this time (368). Alternatively (not shown in FIG. 5), controller 332 may sense for electrical signals when stimulation pulses are expected to check synchronization. For example, controller 332 may close a switch in order to detect any current and/or voltage on the line. In some examples, controller 332 may ground each pulse generator line 344 and any or all electrodes 132 to the system ground within second module 111 (where system ground may be the battery ground i.e. the negative pole of the battery) provided over line 346. In this manner, any residual current or voltage or charge may be removed from second module 111 (e.g. residual charge on DC blocking capacitors, such as capacitors C11, C12, C21, and C22 of FIG. 8) so that any sensed current or voltage must still be output from first module 111. In some examples, controller 332 may look for a voltage or current above a threshold to determine if a stimulation pulse is present since residual current or voltage or charge from a prior stimulation pulse may be expected and/or known and/or present. This threshold may be above the expected residual current, voltage, or charge from a prior stimulation pulse but still low enough to detect any unexpected stimulation pulse (that may be present on the line when the modules are not synchronized) without being triggered by the residuals from a prior stimulation pulse. If the threshold is too low, the residual charge on the capacitor may cause a false trigger of the detector circuit even though the modules are still synchronized. Conversely, if the threshold is too high, unexpected signals from first module 110 may not be detected. In some examples, the stimulation pulses, or residuals, could be configured to always be above and below each other, respectively. This process of sensing for electrical signals from pulse generator 330 is further described in FIGS. 6, 7, and 8 and may include one or both of synchronization detection circuits 402 and 412 of FIG. 8.

If controller 332 does not detect any current or voltage from a stimulation signal during a time when stimulation signals are not expected ("NO" branch of block 370), controller 332 may determine that the modules are synchronized and continue to monitor the AC power signal for other stimulation output (362). However, if controller 332 does detect a stimulation signal still being output by first module 111 ("YES" branch of block 370), controller 332 may determine that the modules are unsynchronized and take steps to correct the synchronization problem between second module 111 and first module 110 (372). As discussed above, corrective action may include controller 332 transmitting a request to processor 328 to cease stimulation output and/or a request to reset the synchronization between the modules and/or ground all pulse generator lines and/or electrodes coupled to second module 111. Once synchronization is corrected, controller 332 may again continue to monitor the AC power signal from first module 110 (362). Thus controller 332 monitors the AC power signal from first module 110 continuously until it detects that the modules are unsynchronized.

Figure 6:
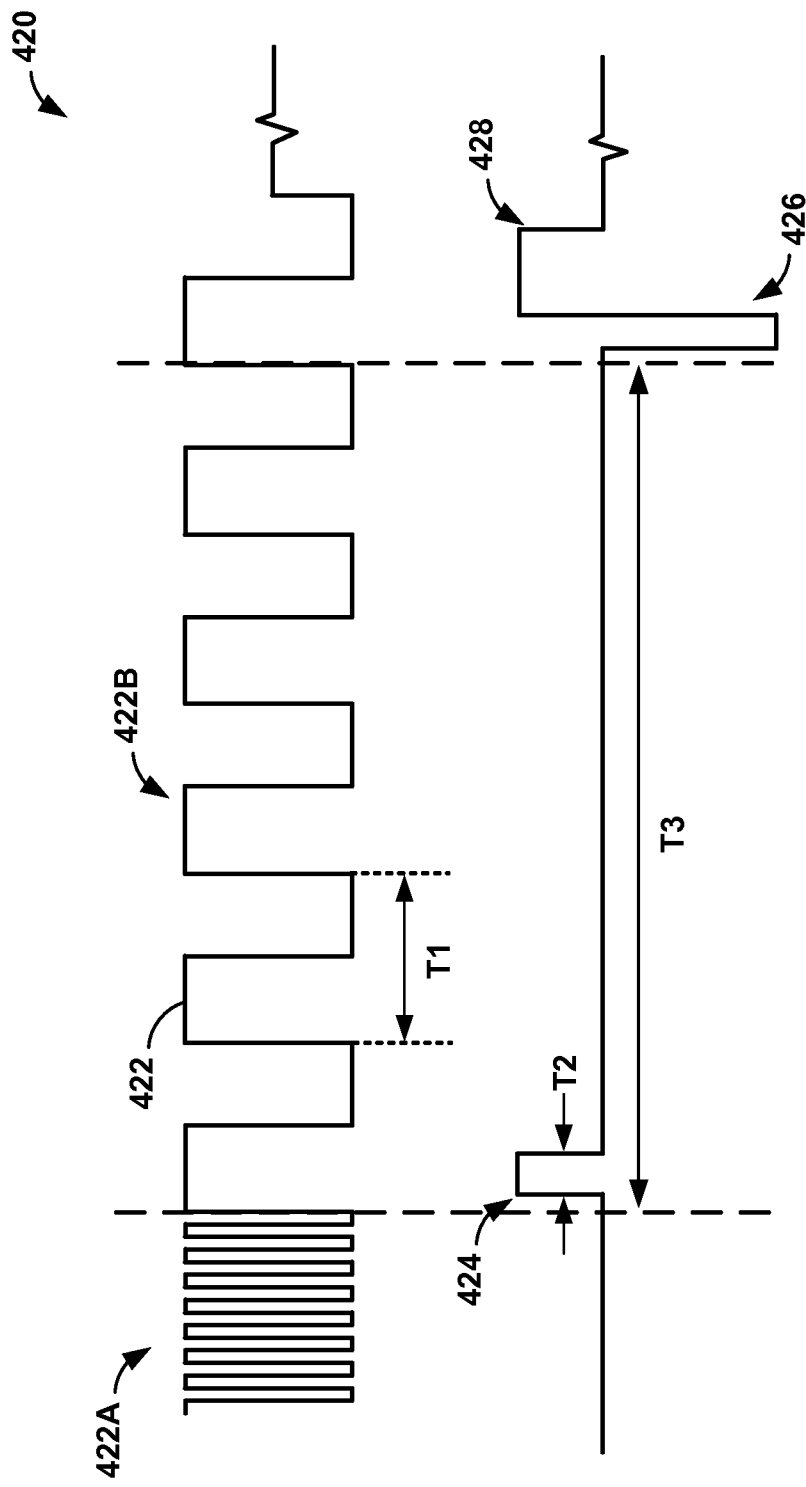
FIG. 6 is a timing diagram of an example AC power signal and synchronization start pulse used to synchronize the start of stimulation pulses between two modules.

FIG. 6 is a timing diagram 420 of an example AC power signal 422 and synchronization start pulse 424 used to synchronize the start of stimulation pulses between two modules such as first module 110 and second module 111. AC power signal 422 may be used as the clock signal and may thus be referred to as a "power/clock" signal. Prior to stimulation being delivered, AC power signal 422 may have a higher frequency as shown in signal portion 422A. The higher frequency signal portion 422A may be an integer multiplier of the lower frequency signal portion 422B that is used during stimulation or an integer multiplier of the stimulation window. Lower frequencies of the clock cycle may provide easier tracking by second module 111 that uses AC power signal 422 to synchronize with first module 110 that is generating AC power signal 422. A lower frequency may also reduce the capacitive switching losses associated with the generation of the "power/clock" signal (e.g. line capacitance, feedthrough capacitance, etc.).

When first module 110 begins to start stimulation, first module 110 (or a pulse generator of first module 110) may generate or output a synchronization start pulse 424 that indicates a stimulation pulse, such as stimulation pulse 426 is coming during the next stimulation window T3. Start pulse 424 may have a pulse width of T2 that is less than one cycle (T1) of AC power signal 422 during the lower frequency signal portion 422B, and the start pulse 424 provides a marker for controller 332 of second module 111 to synchronize with AC power signal 422. Controller 332 of second module 111 may wait for start pulse 424, and in response to detecting start pulse 424, controller 332 begins counting cycles, or pulses, of AC power signal 422. Controller 332 may count the rising edge of AC power signal 422 or other characteristics of AC power signal 422 in other examples to count each cycle of the AC power signal. Controller 332 may receive data from first module 110 indicating the duration of each stimulation window T3 by the number of cycles of AC power signal 422 (e.g., 10, 20, 30, or any other lower or higher number of cycles). Therefore, controller 332 can count the number of cycles to remain synchronized with first module 110 and the timing of when stimulation pulses, such as stimulation pulse 426 and charge neutralization pulse 428, is to occur. As discussed herein, first module 110 may count cycles to determine when stimulation pulses are to be delivered, the duration of biphasic pulses (which may be rounded up to the next integer number of cycles), and/or when stimulation pulses are not to be delivered. In some examples, one or more switches or other components may need to be grounded and/or recharged to maintain operation. Therefore, controller 332 can ground and/or recharge switches or perform other activities during the non-stimulation period (e.g., the period of stimulation window T3 during which no stimulation pulses are scheduled to be delivered) without affecting the delivery of stimulation by counting cycles of AC power signal 422 or any other alternating signal.

Figure 7:
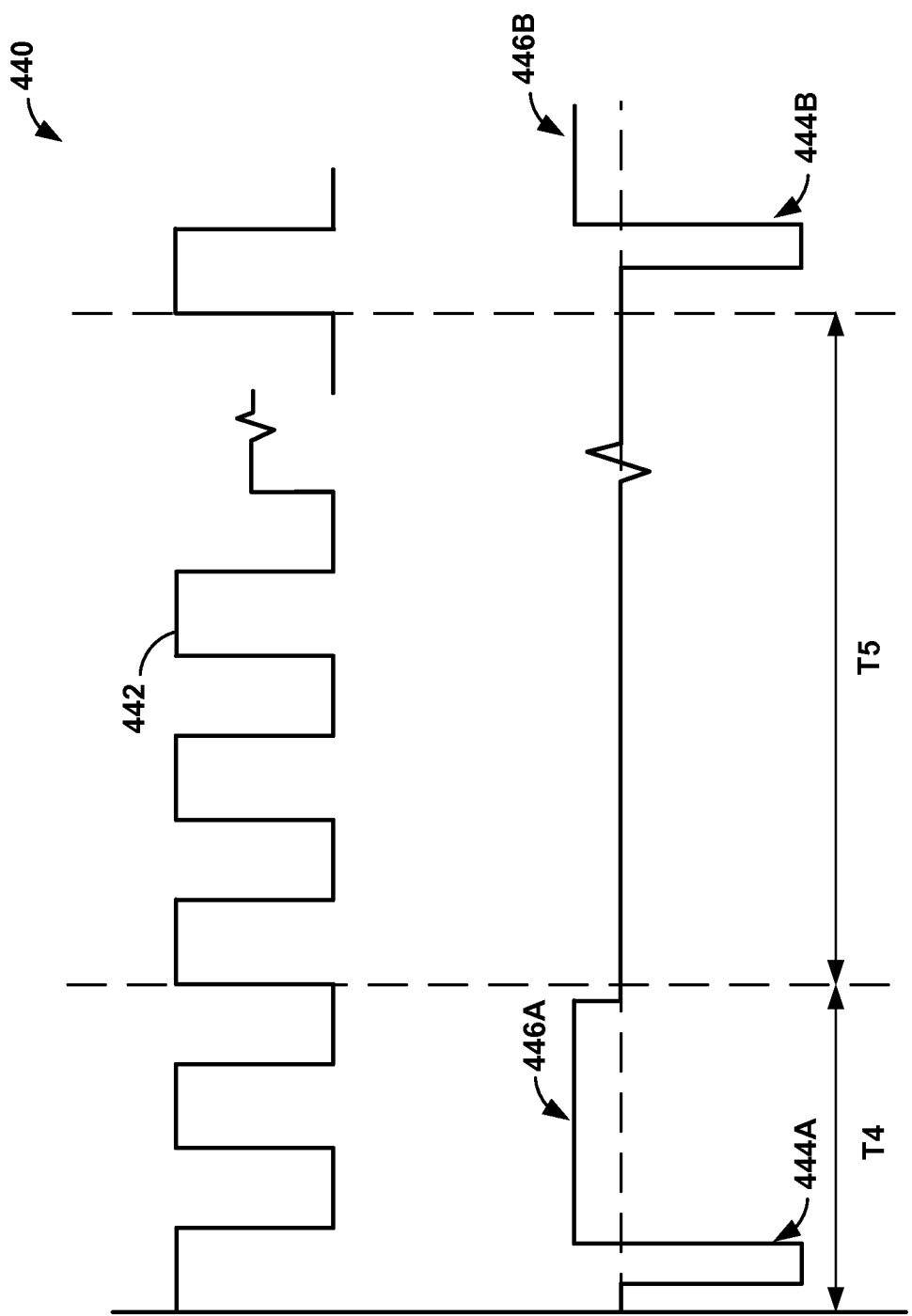
FIG. 7 is a timing diagram of an example AC power signal used to determine a stimulation period and a non-stimulation period.

FIG. 7 is a timing diagram 440 of an example AC power signal 442 used to determine a stimulation period T4 and a non-stimulation period T5 of a stimulation window. As shown in FIG. 7, stimulation pulse 444A and charge neutralization pulse 446A occur within stimulation period T4 that corresponds to two cycles of AC power signal 442. Since controller 332 of second module 111 counts cycles and has instructions indicating that stimulation period T4 lasts for two cycles in this example, controller 332 starts the non-stimulation period T5 at the beginning of the third cycle of AC power signal 442. Non-stimulation period T5 lasts until stimulation pulse 444B and recharge pulse 446B occurs after the predetermined number of cycles of AC power signal 442.

During non-stimulation period T5, controller 332 can perform any functions that need to occur during a period of time in which stimulation pulses are not to be delivered to the patient. For example, controller 332 may ground each line from the respective pulse generator in first module 110 or controller 332 may ground lines 350 coupled to electrodes 132. Controller 332 may also recharge one or more capacitors used as local supply voltage of the switches of the switch matrix in second module 111. These functions and/or other functions may be performed during non-stimulation period T5.

Controller 332 may also use non-stimulation period T5 to check synchronization between first module 110 and second module 111. As described herein, since controller 332 expects that no signals should be present from a pulse generator during non-stimulation period T5, controller 332 may use a synchronization detection circuit, such as detection circuits 402 and/or 412 of FIG. 8, to check the voltage and/or current on each pulse generator line during non-stimulation period T5. If a detection circuit detects current or voltage from a pulse generator of first module 110 during non-stimulation period T5, controller 332 determines that the first module 110 and second module 111 are not synchronized. Controller 332 may then take action such as shutting down second module 111 operation or generating and transmitting an error flag to first module 110. Controller 332 may check for synchronization periodically, such as during a predetermine time period (e.g., once a second) or after a predetermined number of stimulation windows have elapsed (e.g., once per 100 stimulation windows). Controller 332 may also transmit or store in a register a flag indicating the modules are synchronized if the detection circuit does not detect any signals from a pulse generator during the non-stimulation period T5.

Figure 8:
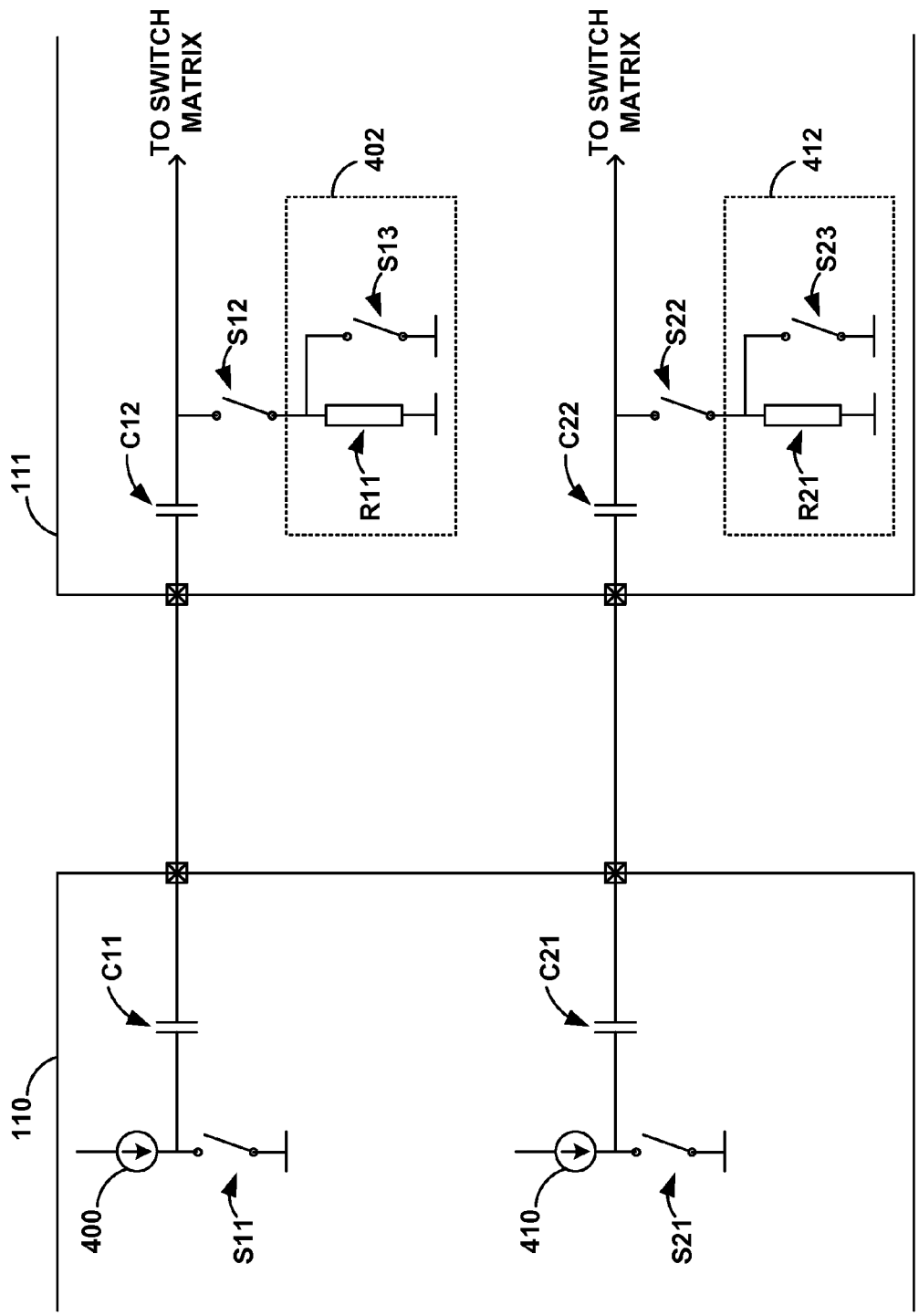
FIG. 8 is a schematic diagram of an example synchronization detection circuit that detects the presence of a signal from a pulse generator.

FIG. 8 is a schematic diagram of example synchronization detection circuits 402 and 412 in second module 111 that detects the presence of a signal from a pulse generator of first module 110. As shown in FIG. 8, first module 110 may include pulse generator 400 and pulse generator 410. Each of pulse generators 400 and 410 may be selectively coupled to ground via switches S11 and S21, respectively. When a pulse generator is not used, its respective switch S11 or S21 may be closed and the line grounded. If the pulse generator line is grounded in second module 111, first module 110 may also ground that line. Current from an (activated) pulse generator 400 may flow through the DC blocking capacitors C11 and C12 to at least some of electrodes 132 connected to the (active) pulse generator line of module 111 via the (not shown) switch matrix. Similarly, current from pulse generator 400 may flow through DC blocking capacitors C21 and C22 to a number of selected electrodes 132 via the (same, not shown) switch matrix.

During delivery of stimulation pulses, synchronization detection circuits 402 and 412 are not coupled to the pulse generator lines because respective switches S12 and S22 are open and not conducting. When grounding the pulse generator lines, switches S12, S13, S22, and S23 are closed. Synchronization detection circuits 402 and 412 are not used to detect signals on the pulse generator lines in this phase. However, when controller 332 is to check synchronization (e.g., during a non-stimulation period), controller 332 closes switches S12 and S22 and leaves switches S13 and S23 open. Therefore, if any current or voltage is present from a pulse generator, that current will generate a voltage on resistor R11 of synchronization detection circuit 402 and/or R21 of synchronization detection circuit 412. A comparator (not shown), for example, may be used to measure this voltage across the respective resistor and transmit an indication of this excess current and/or voltage to controller 332. In other examples, different types of electrical components may be used instead of, or in addition to, resistors R11 and R21. In one example, detection circuit 402 may include resistor R11 with a resistance of 10 k Ohms which would lead to a voltage of plus or minus 100 mV for a current of plus or minus 50 mA, which would also mean that a comparator threshold for detecting current could be plus or minus 500 mV. Other resistances could be used for R11 for other characteristics of the circuit.

Controller 332 may ground each pulse generator line from pulse generators 400 and 410 by closing switches S12, S13, S22, and S23 during each non-stimulation period of a stimulation window. Likewise, processor 328 may ground, in a synchronized fashion, each pulse generator line on the module 110 side by closing switches S11 and S21 during each non-stimulation period. When controller 332 directs unexpected pulse generator line current to resistors R11 and R21 instead to check synchronization using synchronization detection circuits 402 and 412, some current and/or voltage may remain on the pulse generator lines when the next stimulation pulse is generated, because some residual charge on the DC blocking capacitors C11, C12 and/or C21 and C22 from a prior (imbalanced) biphasic stimulation and charge neutralization pulse may not have been dissipated completely during the non-stimulation period when the synchronization detection circuits 402 and 412 are enabled (by opening switches S13 and S23). However, causing some current and/or voltage to remain may not cause problems with therapy delivery or other operations when stimulation is done in the current domain as shown in FIG. 8 by the current pulse generators 400 and 410.

Moreover, any remaining current and/or voltage will be removed from the pulse generator lines during the next non-stimulation period during which all switches S12, S13, S22, and S23 are closed. Although the example of FIG. 8 describes both synchronization detection circuits 402 and 412 being operated simultaneously (e.g., during the same non-stimulation period), controller 332 may check different pulse generator lines at different times in other examples. For example, controller 332 may check for synchronization using synchronization detection circuit 402 in one non-stimulation period and synchronization detection circuit 412 in a subsequent non-stimulation period. Furthermore, different pulse generator lines may have different types of synchronization detection circuit in other examples. In other examples, a single synchronization detection circuit 402 may be used to selectively couple to each of multiple stimulation lines in order to iteratively check each line using the single synchronization detection circuit.

It should be noted that system 100 may not be limited to treatment or monitoring of a human patient. In alternative examples, system 100 may be implemented in non-human patients, e.g., primates, canines, equines, pigs, and felines. These other animals may undergo clinical or research therapies that my benefit from the subject matter of this disclosure.

The techniques of this disclosure may be implemented in a wide variety of computing devices, medical devices, or any combination thereof. Any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The disclosure contemplates computer-readable storage media comprising instructions to cause a processor to perform any of the functions and techniques described herein. The computer-readable storage media may take the example form of any volatile, non-volatile, magnetic, optical, or electrical media, such as a RAM, ROM, NVRAM, EEPROM, or flash memory that is tangible. The computer-readable storage media may be referred to as non-transitory. A server, client computing device, or any other computing device may also contain a more portable removable memory type to enable easy data transfer or offline data analysis.

The techniques described in this disclosure, including those attributed to various modules (e.g., modules 110 and 111) and various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, remote servers, remote client devices, or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an external or implantable device, an integrated circuit (IC) or a set of ICs, and/or discrete electrical circuitry, residing in an implantable device or system, for example.

The techniques described in this disclosure may also be embodied or encoded in an article of manufacture including a computer-readable storage medium encoded with instructions. Instructions embedded or encoded in an article of manufacture including a computer-readable storage medium encoded, may cause one or more programmable processors, or other processors, to implement one or more of the techniques described herein, such as when instructions included or encoded in the computer-readable storage medium are executed by the one or more processors. Example computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or any other computer readable storage devices or tangible computer readable media. The computer-readable storage medium may also be referred to as storage devices.

In some examples, a computer-readable storage medium comprises non-transitory medium. The term "non-transitory" may indicate that the storage medium is not embodied in a carrier wave or a propagated signal. In certain examples, a non-transitory storage medium may store data that can, over time, change (e.g., in RAM or cache).

Various examples have been described herein. Any combination of the described operations or functions is contemplated. These and other examples are within the scope of the following claims.

What is claimed is:

1. A system comprising:
a first module configured to output a therapy; and
a second module distinct from the first module, the second module configured to:
receive, from the first module, an alternating signal;
monitor a characteristic of the alternating signal;
determine, based on the characteristic of the alternating signal, a period of time during which the first module is expected to one of output the therapy or refrain from outputting the therapy; and
check, during the period of time and based on whether the first module is outputting the therapy, a synchronicity between the first module and the second module.

2. The system of claim 1, wherein the second module is configured to sense for output of the therapy from the first module to check the synchronicity, an absence of the output of the therapy during the period of time during which the first module is expected to refrain from outputting the therapy or a presence of the output of the therapy during the period of time during which the first module is expected to output the therapy being indicative of the first module and the second module being synchronized.

3. The system of claim 1, wherein the second module is configured to sense for output of the therapy from the first module to check the synchronicity, a presence of the output of the therapy during the period of time during which the first module is expected to refrain from outputting the therapy or an absence of the output of the therapy during the period of time during which the first module is expected to output the therapy being indicative of the first module and the second module being unsynchronized.

4. The system of claim 1, wherein the alternating signal is an AC power signal from an AC power source.

5. The system of claim 4, wherein the second module is configured to use the AC power signal as a clock signal, wherein the characteristic is a periodic cycle, and wherein the second module is configured to:
count a number of the periodic cycles of the AC power signal;
determine, based on the number, that an expected output from the first module has terminated; and
responsive to determining that the expected output from the first module has terminated, begin the period of time during which the first module is expected to refrain from outputting the therapy.

6. The system of claim 4, wherein the AC power signal is used as a clock signal and the characteristic is a periodic cycle, and wherein the second module is configured to:
count a number of the periodic cycles of the AC power signal;
determine, based on the number, that the first module is outputting therapy; and
responsive to determining that the first module is outputting therapy, begin the period of time during which the first module is expected to output the therapy.

7. The system of claim 5, wherein the first module is configured to output a synchronization start pulse, and wherein the second module is configured to begin counting the number of periodic cycles of the AC power signal upon receiving the synchronization start pulse.

8. The system of claim 4, wherein the therapy is an electrical stimulation signal, and wherein the first module comprises a stimulation pulse generator configured to output the electrical stimulation signal.

9. The system of claim 8, wherein the AC power signal is locked to a stimulation frequency of the electrical stimulation signal.

10. The system of claim 8, wherein the second module is configured to check the synchronicity by sensing, during the period of time, for a characteristic of an electrical stimulation signal on at least one pulse generator line from the first module.

11. The system of claim 4, wherein the first module is configured to add a marker to the AC power signal, the marker indicative of at least one of a beginning of the output of the therapy or an end of the output of the therapy, and wherein the second module is configured to identify the marker as a change in the characteristic of the AC power signal.

12. The system of claim 11, wherein the characteristic is at least one of a frequency of the AC power signal, an amplitude of the AC power signal, or a cycle duration of the AC power signal.

13. The system of claim 11, wherein the marker comprises a clock pulse flip marker.

14. The system of claim 11, wherein the marker comprises a blanking of at least a portion of the AC power signal.

15. The system of claim 1, wherein the therapy comprises delivery of a therapeutic fluid.

16. The system of claim 1, wherein:
the second module is configured to determine that the second module is unsynchronized with the first module and, responsive to determining that the second module is unsynchronized, generate an error flag indicative of the unsynchronization and
the first module is configured to obtain the error flag from the second module and, responsive to obtaining the error flag, perform one or more actions that correct the unsynchronized status between the first and second modules.

17. The system of claim 1, wherein the second module is configured to:
   determine that the second module is unsynchronized with the first module; and
   responsive to the determination that the second module is unsynchronized, transmit a request to the first module to at least one of terminate outputting the therapy or reset the synchronicity of the first and second modules.

18. A method comprising:
   receiving, by a second module distinct from a first module, an alternating signal, wherein the first module is configured to output a therapy;
   monitoring, by the second module, a characteristic of the alternating signal;
   determining, by the second module and based on the characteristic of the alternating signal, a period of time during which the first module is expected to one of output the therapy or refrain from outputting the therapy; and
   checking, by the second module and during the period of time, a synchronicity between the first module and the second module based on whether the first module is outputting the therapy.

19. The method of claim 18, further comprising sensing, by the second module, for output of the therapy from the first module to check the synchronicity, an absence of the output of the therapy during the period of time during which the first module is expected to refrain from outputting the therapy or a presence of the output of the therapy during the period of time during which the first module is expected to output the therapy being indicative of the first module and the second module being synchronized.

20. The method of claim 18, further comprising sensing, by the second module, for output of the therapy from the first module to check the synchronicity, a presence of the output of the therapy during the period of time during which the first module is expected to refrain from outputting the therapy or an absence of the output of the therapy during the period of time during which the first module is expected to output the therapy being indicative of the first module and the second module being unsynchronized.

21. The method of claim 18, wherein the alternating signal is an AC power signal from an AC power source, wherein the second module is configured to use the AC power signal as a clock signal, wherein the characteristic is a periodic cycle, and wherein:
   monitoring the characteristic of the AC power signal comprises counting, by the second module, a number of the periodic cycles of the AC power signal,
   determining the period of time comprises determining, by the second module and based on the number, that an expected output from the first module has terminated and responsive to determining that the expected output from the first module has terminated, beginning the period of time during which the first module is expected to refrain from outputting the therapy.

22. The method of claim 21, further comprising outputting, by the first module, a synchronization start pulse, and wherein the second module is configured to begin counting the number of periodic cycles of the AC power signal upon receiving the synchronization start pulse.

23. The method of claim 18, wherein the therapy is an electrical stimulation signal, and wherein the method further comprises outputting, by a stimulation pulse generator of the first module the electrical stimulation signal.

24. The method of claim 23, wherein checking the synchronicity comprises sensing, by the second module and during the period of time, for an electrical stimulation current on at least one pulse generator line from the first module.

25. The method of claim 18, further comprising:
   adding, by the first module, a marker to the AC power signal, the marker indicative of at least one of a beginning of the output of the therapy or an end of the output of the therapy; and
   identifying, by the second module, the marker as a change in the characteristic of the AC power signal, wherein the characteristic is at least one of a frequency of the AC power signal, an amplitude of the AC power signal, or a cycle duration of the AC power signal.

26. The method of claim 18, further comprising:
   determining, by the second module, that the second module is unsynchronized with the first module;
   responsive to determining that the second module is unsynchronized, generating, by the second module, an error flag indicative of the unsynchronization;
   obtaining, by the first module, the error flag from the second module; and
   responsive to obtaining the error flag, performing, by the first module, one or more actions that correct the unsynchronized status between the first and second modules.

27. A system comprising a first module and a second module, the system comprising:
   means for receiving an alternating signal at the second module distinct from the first module, wherein the first module is configured to output a therapy;
   means for monitoring a characteristic of the alternating signal;
   means for determining, based on the characteristic of the alternating signal, a period of time during which the first module is expected to one of output the therapy or refrain from outputting the therapy; and
   means for checking, during the period of time and based on whether the first module is outputting the therapy, a synchronicity between the first module and the second module.

28. A computer-readable medium storing instructions that, when executed by one or more processors of a second module, cause the one or more processors to:
   receive, from a first module distinct from the second module, an alternating signal, wherein the first module is configured to output a therapy;
   monitor a characteristic of the alternating signal;
   determine, based on the characteristic of the alternating signal, a period of time during which the first module is expected to one of output the therapy or refrain from outputting the therapy; and
   check, during the period of time and based on whether the first module is outputting the therapy, a synchronicity between the first module and the second module.

* * * * *